United States Patent [19]

McHarrie et al.

[11] 4,360,012

[45] Nov. 23, 1982

[54] EXTERNAL FIXATION DEVICES FOR ORTHOPAEDIC FRACTURES

[75] Inventors: John C. McHarrie, Preston; Peter W. Hopcroft, Liverpool, both of England

[73] Assignee: National Research Development Corporation, London, England

[21] Appl. No.: 235,723

[22] Filed: Feb. 18, 1981

[30] Foreign Application Priority Data

Feb. 19, 1980 [GB] United Kingdom ............... 8005579

[51] Int. Cl.³ .................... A61F 5/04; A61B 17/18
[52] U.S. Cl. ........................... 128/92 EB; 128/92 A
[58] Field of Search ............. 128/92 A, 92 EB, 84 R, 128/84 B, 92 R

[56] References Cited

U.S. PATENT DOCUMENTS

| | | | |
|---|---|---|---|
| 1,789,060 | 1/1931 | Weisenbach | 128/92 A |
| 2,143,922 | 1/1939 | Longfellow | 128/92 A |
| 3,669,102 | 6/1972 | Harris | 128/84 R |
| 3,765,034 | 10/1973 | Johnston | 128/92 EB |
| 3,809,074 | 5/1974 | DeMoude | 128/92 A |
| 4,037,592 | 7/1977 | Kronner | 128/92 EB |

FOREIGN PATENT DOCUMENTS

| | | | |
|---|---|---|---|
| 580406 | 8/1958 | Italy | 128/92 A |
| 227453 | 9/1943 | Switzerland | 128/92 EB |

Primary Examiner—Kyle L. Howell
Assistant Examiner—C. W. Shedd
Attorney, Agent, or Firm—Cushman, Darby & Cushman

[57] ABSTRACT

An external fixation device for orthopaedic fractures is provided comprising: a longitudinally-slotted elongate member (20); a plurality of like clamps (30) of two-part form, suitably a longitudinally-bored bolt (31) and nut (38), interconnectable about the member, a first one (31) of such parts serving to clamp a bone pin (10); and a drill guide (40) suitably of split bush form adapted for interchange with one (31) of said clamp parts in connection with the other clamp part (38); each clamp and guide being adapted when connected with the member respectively to align a bone pin and drill, which can be the pin itself, in a common predetermined direction relative to the member. This device facilitates parallel alignment of an array of bone pins by use of the guide and clamps in successive connection with the member to determine a common frame of reference.

The split bush guide preferably defines a passageway (46) which is diametrically enlarged (47) at its end remote from the member to allow entry of the threaded portion normally provided on a bone pin, this enlargement being exposed by lateral aperturing (48) of the bush.

The device can be unilateral in overall form, or bilateral by the provision of a further member and associated set of clamps.

3 Claims, 5 Drawing Figures

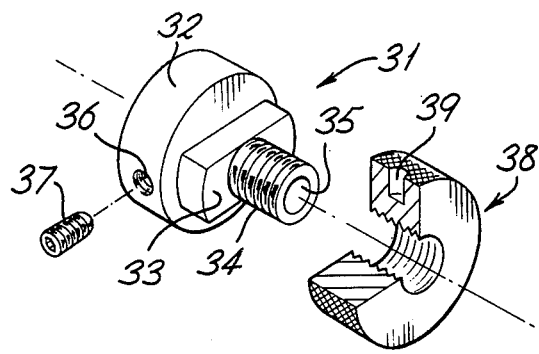
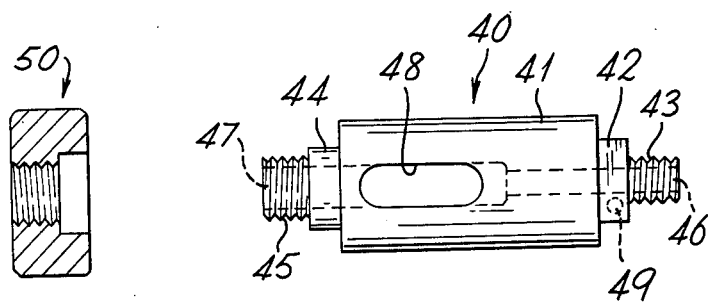
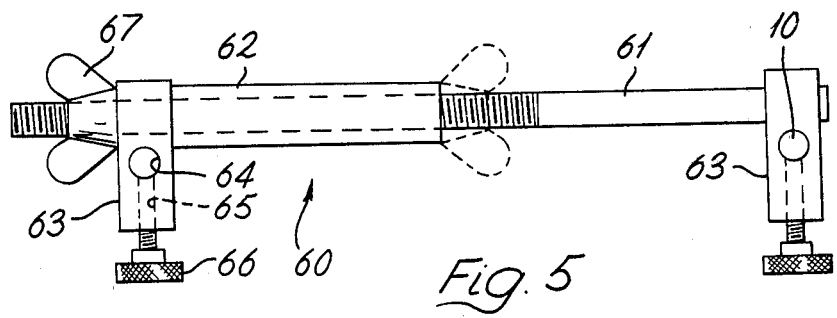

EXTERNAL FIXATION DEVICES FOR ORTHOPAEDIC FRACTURES

This invention concerns external fixation devices for orthopaedic fractures and more particularly such devices of the kind involving a range of components which are variably connectable with each other and with the fragments of a fractured bone by way of bone pins to form a support holding the bone fragments in a desired positional relationship for the purposes of reunion.

Some such devices have been designed to cater for a considerable variety of fracture and related situations. These devices involve an extensive range of components, including universal couplings, and are relatively complex in form and usage, and they are correspondingly expensive.

Other forms of the above kind of devices have been designed for use in a lesser variety of, but nevertheless commonly occurring situations, particularly situations involving fractures in the long bones of the limbs. These last devices are relatively simpler but are still not fully satisfactory in all respects and normally suffer from one or more disadvantages including high weight, high cost, and complication in usage. One particular complication is that these simpler devices usually require the location of a plurality of bone pins in a parallel array, and this requirement is commonly met by the use of a separate, cumbersome multiple-drilling jig.

An object of the present invention is to reduce the last mentioned disadvantage and, to this end, there is provided an external fixation device for orthopaedic fractures comprising: a longitudinally-slotted elongate member; a plurality of like clamps of two-part form interconnectable about said member by way of a slot therein, a first one of such parts serving to clamp a bone pin; and a drill guide adapted for interchange with one of said clamp parts in connection with the associated other part of each clamp; said clamp and guide being adapted, when connected to said member, respectively to align a bone pin and drill bit in a common predetermined direction relative to said member.

It will be appreciated that the proposed device is advantageous in facilitating parallel alignment of an array of bone pins by use of the guide and clamps in successive connection with the member to determine a common frame of reference. This applies both when a separate drill bit is used or, as is more conventional, self-boring bone pins are used. Also it will be evident that the device can be of unilateral form involving a single elongate member for the application of pins from one side of a bone only, or of bilateral form involving two members for location along opposite sides of a bone in association with pins passing wholly through the relevant limb. In this last case the maintenance of a parallel alignment for the pins is particularly important to ensure registration with the opposed members and clamps.

In a presently preferred form of the proposed device, the clamp comprises a longitudinally-bored bolt and a nut, with the bolt having a threaded transverse bore in its head to allow securement by a screw of a bone pin passing through its longitudinal bore. Also in this preferred form, the guide comprises a split bush defining a guide passageway which is diametrally enlarged over one end portion, this bush being threadably engageable at its one end with the clamp nut and at its other end with a further nut. The enlarged portion of the bush passageway is intended to accommodate the threaded portion conventionally provided along the centre of a bone pin, and the bush halves are suitably laterally apertured over the inner end of this passage enlargement to allow visual monitoring of the bone pin location therein. The clamp bolt and guide bush are each preferably formed with diametral ribs to engage in a slot of the elongate member and thereby prevent mutual rotation.

Regarding the form of the elongate member: this is preferably a bar of rectangular cross-section with a sequence of slots therealong through its narrower dimension. This form optimises strength while affording wide variation in the choice of clamp location and, of course, reducing the weight of the member. In this last respect additional gain is achieved by making the member of a light, economic metal such as an aluminium alloy.

The above-mentioned presently preferred form of the device will now be more fully described, to further clarify the invention by way of example, with reference to the accompanying drawings in which:

FIG. 2 is a partially sectioned, exploded perspective view of a clamp of FIG. 1;

FIGS. 3 and 4 are respectively a longitudinal view and sectional view of two parts of a guide for use with the embodiment of FIG. 1; and FIG. 5 is a view of an additional mechanism for use with the device of FIG. 1.

Figure 1:
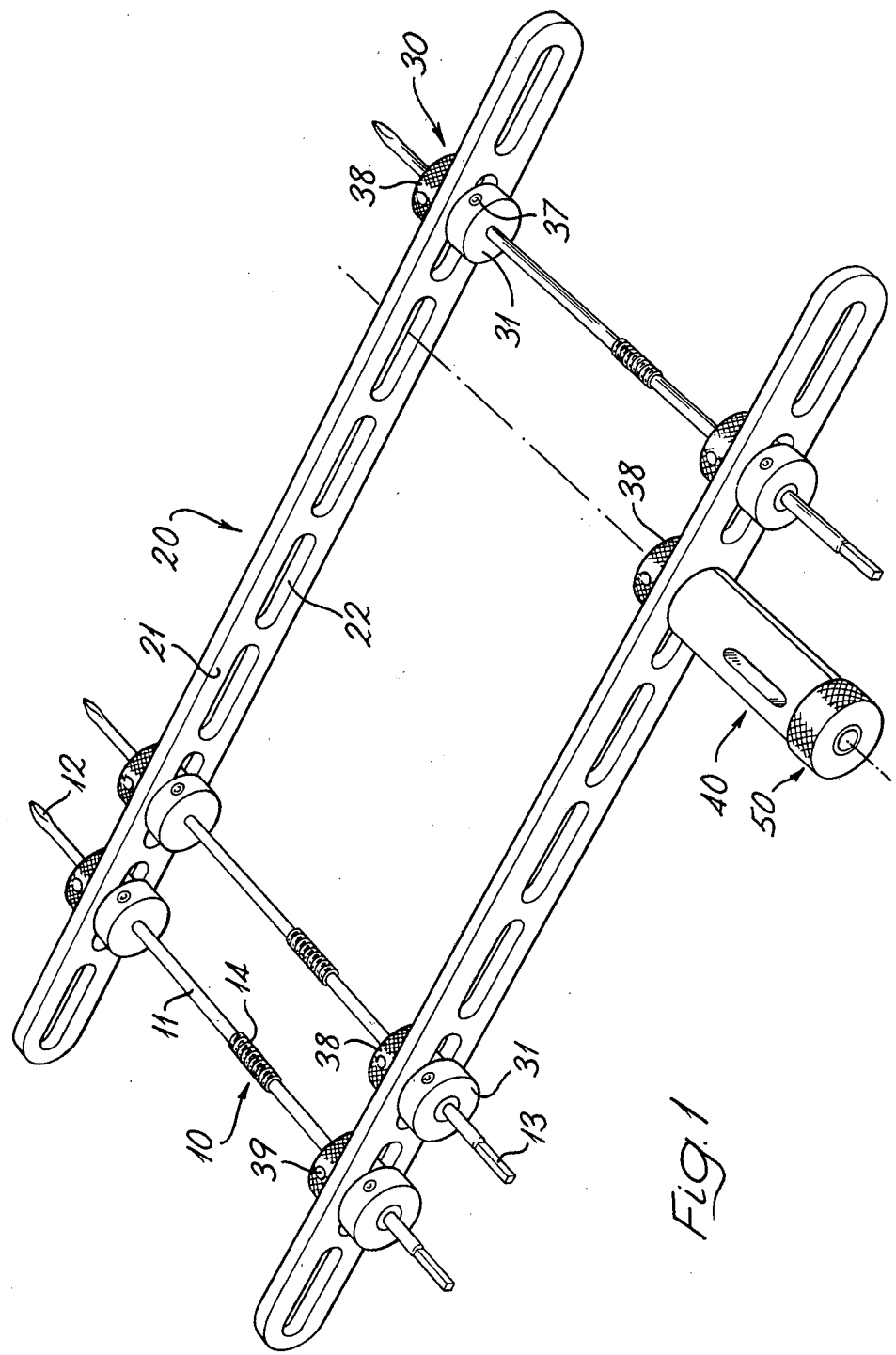
FIG. 1 illustrates in perspective view one embodiment of the device.

The illustrated device of FIG. 1 is shown in use with a parallel array of four bone pins 10, the device being of bilateral form comprising two like elongate members 20 between which each pin extends by way of clamps 30.

The pins are of a standardised conventional form having a circular-section shaft 11 which is tapered and flattened to serve as a bit 12 at one end, shaped to polygonal cross-section at the other end 13 for engagement in a drill chuck, and having a raised threading over a central portion 14.

The members 20 are each in the form of a bar 21 of rectangular cross-section having a sequence of equal longitudinally-extending slots 22 uniformly spaced therealong, the slots passing through the narrower dimensions of the bar. The bar is made of an aluminium alloy.

The clamps 30 are each of two-part form comprising a bolt 31 and nut 38 shown in more detail in FIG. 2. These components are also suitably made of the aluminium alloy. The bolt 31 is composed of three successive portions, namely, a head 32, a diametral rib 33 across the underface of the head, and an externally threaded shaft 34. These portions are longitudinally bored to provide a main axial through-bore 35. In addition, the head is formed with at least one threaded radial bore 36, extending from its side through to the main bore. The main bore of the bolt is of such a diameter as to receive the bone pin shaft 11 in a sliding fit, but not the threaded portion 14 of the pin, and a pin can be secured therein by application of an allen screw 37 applied to a radial bore 36 as shown in FIG. 1. The bolt shaft 34 is of such a diameter to pass through a bar slot 22, and the bolt rib 33 is dimensioned to seat in such a slot allowing non-rotatable sliding engagement of the bolt therein with the shaft 34 projecting therefrom.

The nut 38 of the clamp is dimensioned to threadably engage around the bolt shaft and thereby secure the clamp to a bar 20 with the shaft projecting through a slot thereof as just described. The nut is knurled to facilitate handling, and tightening is enhanced by the provision of holes 39 in the nut side surface for cooperation with a suitable lever.

The use of the device as so far described is largely self-evident in that a fractured long bone in a limb can be appropriately manipulated and reduced to a desired configuration for re-union and held in this configuration by the application of bone pins in a parallel array through the limp and securement of such an array as shown in FIG. 1 with the members 20 extending along opposite sides of the limb. Alternatively, it may be appropriate in some conditions to use only one member 20 alongside the limb to locate and secure the pins. In application of the pins the device is used with successive interchange of a guide for the bolts 31 associated with one bar, the guide being formed by parts as shown in FIGS. 3 and 4 in successive connection with the nuts 38 for those bolts.

The relevant guide is of split bush form composed of two mirror-image bush halves and an additional nut. FIGS. 3 and 4 respectively show the bush 40 and nut 50, the bush being illustrated with both halves in engagement along a medial plane parallel to that of FIG. 3.

The bush 40 has a main body portion 41 of elongated cylindrical form continuing at one end into a rib 42 and then an externally threaded shaft portion 43 in similar manner to the bolt 31, and at the other end into a short portion 44 of reduced diameter and then a further externally threaded shaft portion 45 of yet further reduced diameter. The bush is bored wholly axially therethrough with a bore 46 which extends over the end region including the rib 42 and the adjacent main body portion, this bore being counterbored at 47 to an increased diameter over the remaining length of the bush. The bore 46 receives the bone pin shaft in a sliding fit to guide the same, and the counterbore 47 is a clearance fit for the threaded portion for the pin. The bush is additionally formed with diametrally-opposed longitudinal slots 48, disposed one in each bush half and extending over the major part of the counterbore 47 within the main body portion 41, these slots exposing the counterbore to the bush exterior.

As so far described the bush is composed of two exact mirror-image halves, but the halves differ in one respect, namely the respective provision of studs and complementary sockets on their mutually abutting faces to facilitate registration. One pair of studs and sockets is denoted at 49 on the halves of rib 42.

The nut 50 is complementary to the portions 44 and 45 of the bush.

In use of the illustrated guide, the bush halves are registered, held together by connection of the nut 50, and then passed, with the shaft 43 leading, to locate the rib 42 in an appropriate slot of one of the members, whereat the assembled bush is secured in position by a nut 38 applied to the projecting shaft 43. A bone pin can then be applied through the bush and drilled into a bone of a limb alongside which a member 20 has been located with the guide projecting outwardly therefrom. This drilling is interrupted when the pin threaded portion approaches the end of the counterbore 47 nearer to the member 20, this being judged visually through the slots 48, the nut 50 and the bush are then removed, drilling continued to fully locate the pin with its threaded portion in the bone, and a bolt 31 is passed over the trailing end of the pin and connected with the nut 38 to allow securement of the pin by the screw 37 of the bolt. This procedure is repeated for each pin to be used and it will be appreciated that, after the first pin is secured, further pins are constrained by the guide and associated member 20 to assume a mutually parallel disposition.

A further member 20 can then be located alongside the limb remotely from the first such member, this further member being connected with the pins by way of further clamps 30 as shown in FIG. 1.

It may well be appropriate in use of the invention to apply compression or distraction across a fracture by way of the bone pins and this can be effected by way of a screw mechanism connected between adjacent pins respectively located on opposite sides of the fracture. One such mechanism is a so-called Charnley clamp as illustrated in FIG. 5 and denoted generally as 60.

The mechanism 60 includes a rod 61 threaded over part of its length from one end, and a tube 62 which is a clearance fit over the rod. The non-threaded end of the rod has a lateral extension in the form of a disc 63 connected thereto, and another such disc is similarly connected to one end of the tube. Each disc is connected to its rod or tube with their axes in off-set parallel disposition, each disc has a diametral bore 64 therethrough to receive a bone pin shaft in a clearance fit, and each disc has a radial, threaded bore 65 communicating with the diametral bore and receiving a bolt 66 to secure a pin passing through the latter bore. The remaining component of the mechanism is a wing nut 67 engageable with the rod thread.

Use of this mechanism with the device is effectively illustrated in FIG. 5. In this case, the tube is passed over the threaded rod, the disc diametral bores are passed over respective ones of the bone pins between which force is to be applied, all of the pins on at least one side of the relevant fracture being slidably coupled with the associated member or members 20 by slight loosening of their bolts 31 and nuts 38, the pins are secured to the discs by tightening bolts 65, and then the wing nut is engaged and tightened on the free threaded end of the rod, whereafter the pins can be secured with the member or members 20 and the mechanism removed. This procedure clearly applies compressive force across the fracture. Distraction force can be applied by relocating the wing nut on the inner end of the rod thread relative to the tube, as indicated in broken outline.

We claim:

1. An external fixation device for orthopaedic fractures comprising:
   a longitudinally-slotted elongate member;
   a plurality of bone pin clamps having like two-part form, each said clamp connected about said member by way of a slot therein and at successive positions along said member, and each clamp serving to secure a respective bone pin passing therethrough;
   each said clamp including a longitudinally-bored bolt having a rib formation at one end thereof non-rotatably engaged in said slot from one side of said member, and a first nut threadably engaged with said bolt one end from the other side of said member;
   and a single drill guide successively interchangeable with each of said clamp bolts to align the respective bone pins in parallel manner in predetermined relation with said member;

said guide including an axially split bush formed of two halves having respective cooperable detent and indent formations engaged to register the halves, said bush being externally threaded at one end for successive engagement with each said clamp first nut and having a rib formation at said one end of said bush for non-rotatable engagement in said slot, and a second nut threadedly engaged around said bush other end.

2. A device according to claim 1 wherein the passageway through said drill guide bush is diametrally enlarged over said other end thereof.

3. A device according to claim 2 wherein said passage, where diametrally enlarged, is exposed by lateral aperturing of said bush.

* * * * *